(12) United States Patent
Metzger et al.

(10) Patent No.: US 6,589,283 B1
(45) Date of Patent: Jul. 8, 2003

(54) ELONGATED FEMORAL COMPONENT

(75) Inventors: Robert Metzger, Walkarusa, IN (US); Troy Hershberger, Warsaw, IN (US)

(73) Assignee: Biomet, Inc., Warsaw, IN (US)

( * ) Notice: Subject to any disclaimer, the term of this patent is extended or adjusted under 35 U.S.C. 154(b) by 7 days.

(21) Appl. No.: 09/855,939

(22) Filed: May 15, 2001

(51) Int. Cl.[7] ................................. A61F 2/38
(52) U.S. Cl. ................. 623/20.35; 623/20.36; 623/20.32; 623/20.21; 623/20.19; 623/20.14; 623/13.12; 606/88; 606/89
(58) Field of Search ............... 606/96, 89, 88, 606/87, 80; 623/20.35, 20.32, 20.29, 20.28, 20.23, 20.21, 20.19, 20.18, 20.15, 20.14, 13.12

(56) References Cited

U.S. PATENT DOCUMENTS

| | | | | |
|---|---|---|---|---|
| 4,207,627 A | * | 6/1980 | Cloutier | 623/20.21 |
| 4,224,697 A | * | 9/1980 | Murray et al. | 623/20.25 |
| 4,731,086 A | * | 3/1988 | Whiteside et al. | 623/20.16 |
| 4,936,847 A | | 6/1990 | Manginelli | |
| 4,950,298 A | * | 8/1990 | Gustilo et al. | 623/20.15 |
| 5,152,797 A | * | 10/1992 | Luckman et al. | 623/20.16 |
| 5,226,915 A | | 7/1993 | Bertin | |
| 5,458,645 A | * | 10/1995 | Bertin | 128/898 |
| 5,609,645 A | * | 3/1997 | Vinciguerra | 623/20.28 |
| 5,702,464 A | * | 12/1997 | Lackey et al. | 623/20.32 |
| 5,776,201 A | | 7/1998 | Colleran et al. | |
| 5,800,552 A | * | 9/1998 | Forte | 623/20.27 |
| 6,165,223 A | * | 12/2000 | Metzger et al. | 623/20.14 |
| 6,190,415 B1 | * | 2/2001 | Cooke et al. | 623/20.31 |
| 6,319,283 B1 | * | 11/2001 | Insall et al. | 623/20.24 |
| 6,379,388 B1 | * | 4/2002 | Ensign et al. | 623/20.21 |

FOREIGN PATENT DOCUMENTS

WO   WO90/14806   12/1990

* cited by examiner

*Primary Examiner*—David J. Walczak
*Assistant Examiner*—Azy Kokabi
(74) *Attorney, Agent, or Firm*—Harness, Dickey & Pierce, P.L.C.

(57) ABSTRACT

The invention relates to a knee joint prosthesis system adapted to replace the articulating knee portion of a femur and a tibia. The knee joint prosthesis system includes a first femoral component and a second femoral component. The first femoral component includes a first femoral engagement region and a first condylar portion having a first femoral bearing surface. The first femoral engagement region is operable to engage a resecting engagement surface of the femur and the first condylar portion includes a first posterior region having a first thickness. The second femoral component includes a second femoral engagement region and a second condylar portion having a second femoral bearing surface. The second femoral engagement region is operable to engage the resected engagement surface of the femur and the second condylar portion includes a second posterior region having a second thickness. The second thickness is larger than the first thickness and the first femoral engagement region is substantially the same as the second femoral engagement region, whereby a surgeon may select either the first femoral component or the second femoral component for attachment to the femur.

18 Claims, 5 Drawing Sheets

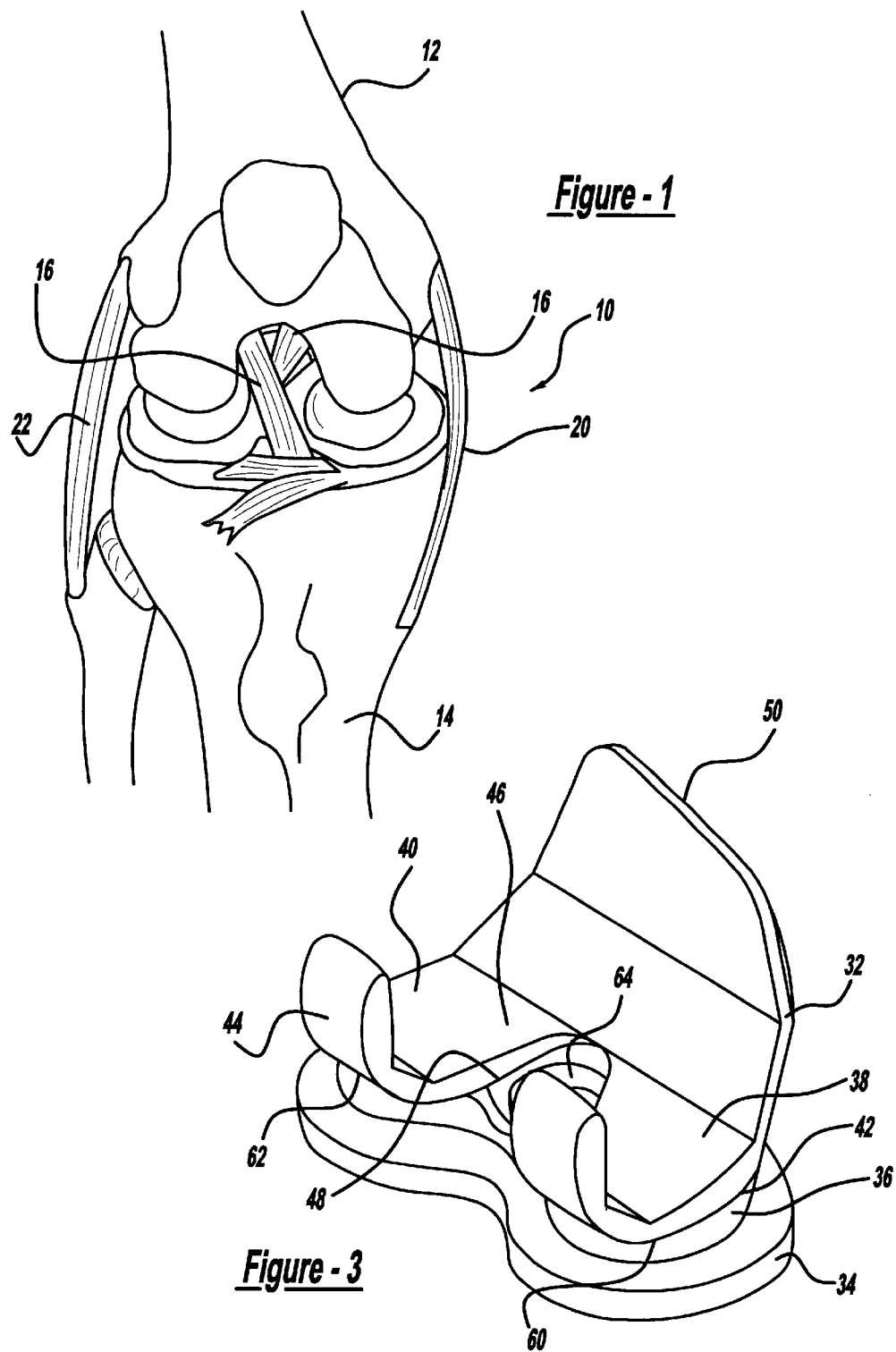

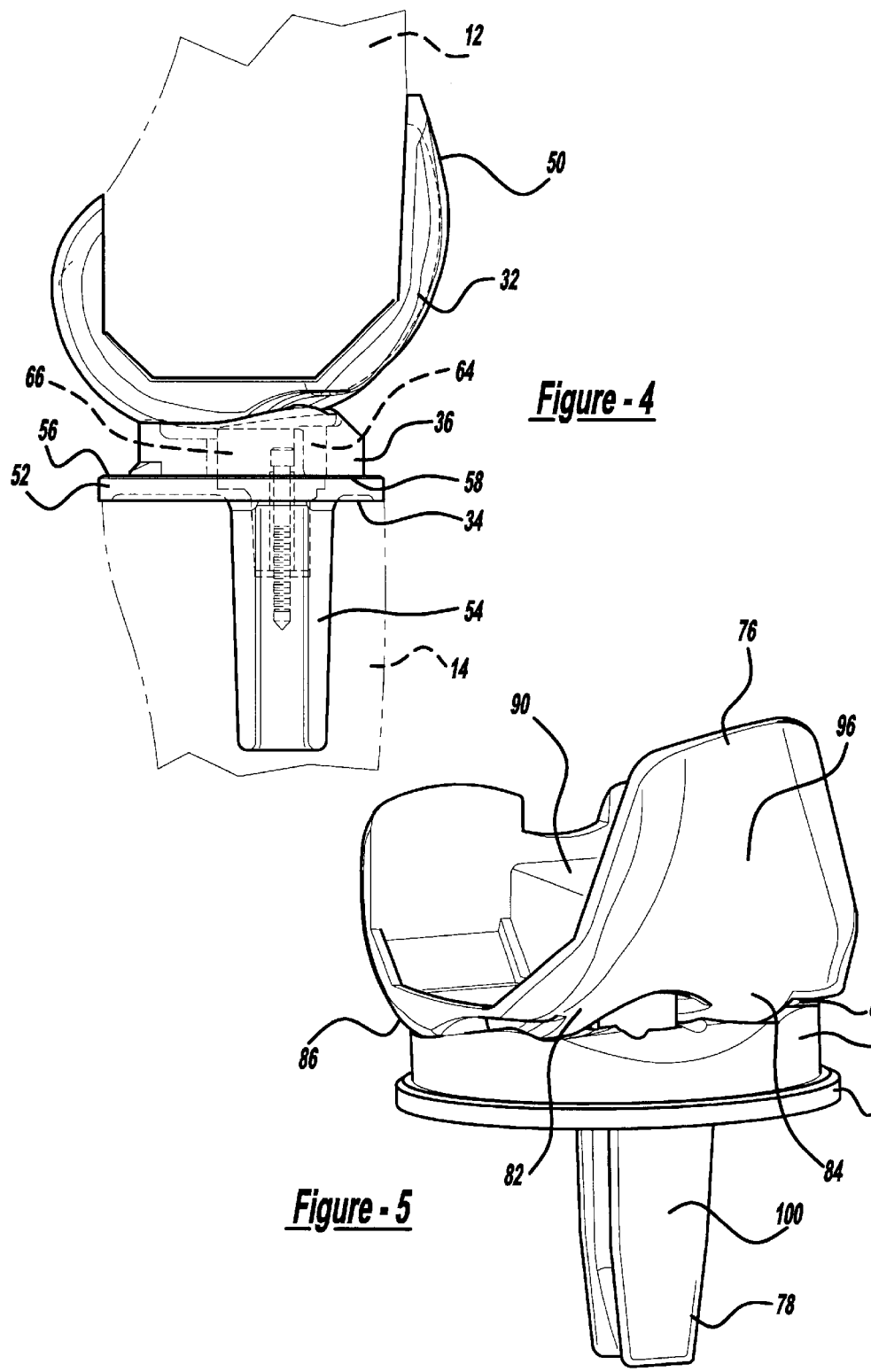

ELONGATED FEMORAL COMPONENT

BACKGROUND OF THE INVENTION

1. Field of the Invention

The present invention relates generally to a knee joint prosthesis, which replaces the articulating knee portion of the femur and tibia, and more particularly, to a knee joint prosthesis system, which includes elongated femoral components for posterior stabilized and fully constrained applications.

2. Discussion of the Related Art

The knee joint is a complex articulating structure. The knee joint includes a femur, which articulates with a tibia, and a patella, which acts as a protective shield for the articulating knee joint. The knee joint also includes soft tissue ligaments, which extend on the medial and lateral side of the knee joint, which are generally referred to as collateral ligaments and ligaments which cross within the knee joint generally referred to as an anterior cruciate ligament and a posterior cruciate ligament.

A knee joint prosthesis typically comprises a femoral component and a tibial component. The femoral component and the tibial component are designed to be surgically attached to the distal end of the femur and the proximal end of the tibia, respectively. The femoral component is further designed to cooperate with the tibial component in simulating and articulating motion of an anatomical knee joint.

The motion of a natural knee joint is kinematically complex. During a relatively broad range of flexion and extension, the articular or bearing surfaces of a natural knee experience rotation, medial and lateral angulation, translation in the sagittal plane, rollback and sliding. Knee joint prostheses, in combination with ligaments and muscles, attempt to duplicate this natural knee motion, as well as absorb and control forces generated during the full range of flexion. Depending on the degree of damage or deterioration of the knee tendons and ligaments, it may be necessary for a knee joint prosthesis to eliminate one or more of these motions in order to provide adequate stability.

To provide for these stabilities, knee joint prostheses generally have different levels of constraint. For example, cruciate retaining (CR) knee joint prostheses provide the least level of constraint, posterior stabilized (PS) knee joint prostheses provide an intermediate level of constraint, while fully constrained knee joint prostheses provide the highest level of constraint upon the kinematic motions of a knee joint. In some situations, a patient may initially require a less constrained knee joint, such as a cruciate retaining (CR) or posterior stabilized (PS) knee joint prosthesis. The patient may later require a fully constrained knee joint prosthesis because the patient is exhibiting instability. Moreover, during the surgical procedure, a surgeon may initially wish to implant a cruciate retaining type knee joint prosthesis and subsequently realize that a posterior stabilized or a fully constrained knee joint prosthesis is required, which may lead to additional surgical resections, as well as surgical time and cost.

There is much debate among knee surgeons regarding whether to resect the posterior cruciate ligament (PCL). Some surgeons will preserve the PCL if at all possible. Many other surgeons will selectively preserve the PCL. Some surgeons who sacrifice the PCL may rely on flexion-extension balance and tibial inserts for stability. Other surgeons may advocate PCL excision and substitute for the ligament using a posterior stabilized (PS) knee joint prosthesis.

PCL substitution with a posterior stabilized (PS) knee joint prosthesis generally requires the removal of intercondylar bone for the PS knee joint prosthesis. As a consequence, there is increased bone removal compared with PCL preservation and the use of a cruciate retaining CR knee joint prosthesis. It has also been suggested in the literature that removal of intercondylar bone may predispose to intercondylar bone fracture. Additionally, resection of the PCL results in an increase in flexion gap relative to extension gap. In contrast to this, the surgical technique for PCL retention is sometimes less forgiving than for PCL substitution because, in addition to balancing the flexion and extension gaps and collateral ligaments, balancing of the PCL is required. In some patients, the PCL may be absent or incompetent and balancing is, therefore, difficult to achieve.

Despite the PCL debate, there appears to be no clear advantage to PCL preserving or substituting designs with regard to knee joint prosthesis. Clinical results appear to indicate that success of knee joint prostheses is associated with factors other than whether or not the PCL is preserved.

Normally, a surgeon will preoperatively select a certain type of knee joint prosthesis. However, the surgeon may find interoperatively in trial, that the preselected prosthesis may not provide the best function of the knee joint and that surgical adjustments in the knee joint are required. In this case, the surgeon is faced with several disadvantages, which will be illustrated in the examples below.

In one example, the surgeon may decide preoperatively to use a posterior stabilized PS knee joint prosthesis. Then, interoperatively in trial if the surgeon determines that the increase in flexion gap is minimal, the surgeon may decide not to compensate for the increased flexion gap. However, if the increase in flexion gap is greater than the surgeon had interoperatively evaluated it to be, the knee joint may postoperatively become loose in flexion which can affect the stability and balance of the implanted knee joint. Additionally, the remaining ligaments in the patients knee joint may become lax and this can also affect stability and wear in the prosthetic knee joint. This is because there may be more edge loading or rotation in the bearing of the prosthetic knee joint and that may be disadvantageous for the knee joint prosthesis patient in the long term.

In another situation, the surgeon may decide interoperatively to change from a cruciate retaining (CR) knee joint prosthesis to a posterior stabilized (PS) knee joint prosthesis. However, by removing the PCL, the flexion gap will increase and further bone resection may be required. To address this situation, the surgeon may opt to use a larger femoral component. However, the larger femoral component places the articulation point of the knee joint in the same position relative to the anterior cortex and by using the larger femoral component, it will occupy the region of the extra flexion gap. But the width in the medial-lateral (ML) portion increases with the larger femoral component. This can restrict flexion of the knee, which might not be acceptable to an active knee joint prosthesis patient.

In still another example, where the surgeon decides to interoperatively change from a cruciate retaining (CR) knee joint prosthesis to a posterior stabilized (PS) knee joint prosthesis and the femur has already been resected to form the engagement surface, the surgeon will generally be unable to use a larger femoral member without using a posterior augment. Currently, many surgeons are reluctant to use a posterior augment in the knee for fear of future deterioration of the knee joint. Additionally, if there is an increase in flexion gap, the surgeon may decide to insert a thicker bearing to decrease the flexion gap. The end result is that in extending the knee position, the patient may complain of a "tight knee". Anticipating this, a surgeon may resect the femoral distal bone and move the femoral component up the leg to obtain an equal gap in flexion and extension. However, this may create problems with patella tracking in the knee joint and the knee joint prosthesis patient may find this to be disadvantageous.

What is needed then is a knee joint prosthesis system which does not suffer from the above mentioned disadvantages. This, in turn, will permit interoperative options for selecting a cruciate retaining (CR) knee joint prosthesis, a posterior stabilized (PS) knee joint prosthesis or a fully constrained knee joint prosthesis where the posterior stabilized and the fully constrained knee joint prosthesis compensate for the increased flexion gap due to resection of the posterior cruciate ligament, reduce or eliminate the requirement for further bone resection irrespective of the type of constraint knee joint prosthesis selected, thereby reducing surgical time, cost and complexity, and further provide selection between the various constrained knee joint prostheses without having to oversize or undersize any of the particular components of the knee joint prosthesis. It is, therefore, an object of the present invention to provide an elongated femoral component in a knee joint prosthesis system that achieves the above-identified advantages.

SUMMARY OF THE INVENTION

In a first preferred embodiment, a knee joint prosthesis system adapted to replace the articulating knee portion of a femur and a tibia includes a first femoral component and a second femoral component. The first femoral component includes a first femoral engagement region and a first condylar portion having a first femoral bearing surface. The first femoral engagement region is operable to engage a resected engagement surface of the femur and the first condylar portion includes a first posterior region having a first thickness. The second femoral component includes a second femoral engagement region and a second condylar portion having a second femoral bearing surface. The second femoral engagement region is operable to engage the resected engagement surface of the femur and the second condylar portion includes a second posterior region having a second thickness. The second thickness is larger than the first thickness and a first femoral engagement region is substantially the same as the second femoral engagement region, such that a surgeon may select one of the first femoral component and the second femoral component for attachment to the femur.

In another preferred embodiment, a knee joint prosthesis adapted to replace the articulating knee portion of a femur and a tibia includes a cruciate retaining (CR) femoral component and a posterior stabilized (PS) femoral component. The cruciate retaining (CR) femoral component includes a first femoral engagement region and a first condylar portion having a first femoral bearing surface. The first femoral engagement region is operable to engage a resected engagement surface of the femur and the first condylar portion includes a first posterior region having a first thickness and a first distal region having a second thickness where the first thickness is substantially equal to the second thickness. The posterior stabilized (PS) femoral component includes a second femoral engagement region and a second condylar portion having a second femoral bearing surface. The second femoral engagement region is operable to engage the resected engagement surface of the femur and the second condylar portion includes a second posterior region having a third thickness and a second distal region having a fourth thickness. The third thickness is greater than the fourth thickness and the first femoral engagement region is substantially the same as the second femoral engagement region. This enables a surgeon to select the cruciate retaining (CR) femoral component or the posterior stabilized (PS) femoral component, whereby the posterior stabilized (PS) femoral component will accommodate for an increased flexion gap upon resection of a posterior cruciate ligament.

In yet another preferred embodiment, a method for implanting a femoral component to a femur having a resected engagement surface from a knee joint prosthesis system is provided. This method includes resecting the femur to provide the resected engagement surface and providing a first femoral component and a second femoral component. The first femoral component includes a first condylar portion which includes a first posterior region having a first thickness and a second femoral component includes a second condylar portion having a second posterior region having a second thickness where the second thickness is greater than the first thickness. The method further includes interoperatively determining if a posterior cruciate ligament should be removed and if the posterior cruciate ligament is retained selecting the first femoral component and if the posterior cruciate ligament is removed selecting the second femoral component which will accommodate for an increased flexion gap upon resection of the posterior cruciate ligament.

The use of the present invention provides a knee joint prosthesis system which includes an elongated femoral component to accommodate for an increased flexion gap upon resection of a posterior cruciate ligament. As a result, the aforementioned disadvantages associated with the currently available knee joint prosthesis have been substantially reduced or eliminated.

BRIEF DESCRIPTION OF THE DRAWINGS

Still other advantages of the present invention will become apparent to those skilled in the art after reading the following specification and by reference to the drawings in which:

FIG. 1 is a perspective view of a natural anatomical knee joint;

FIG. 3 is a perspective view of the cruciate knee joint according to the teachings of the present invention;

FIG. 4 is an assembled side view of the cruciate knee joint according to the teachings of the present invention;

FIG. 5 is a perspective view of the posterior stabilized (PS) knee joint prosthesis according to the teachings of the present invention;

DETAILED DESCRIPTION OF THE PREFERRED EMBODIMENTS

Figure 2C:
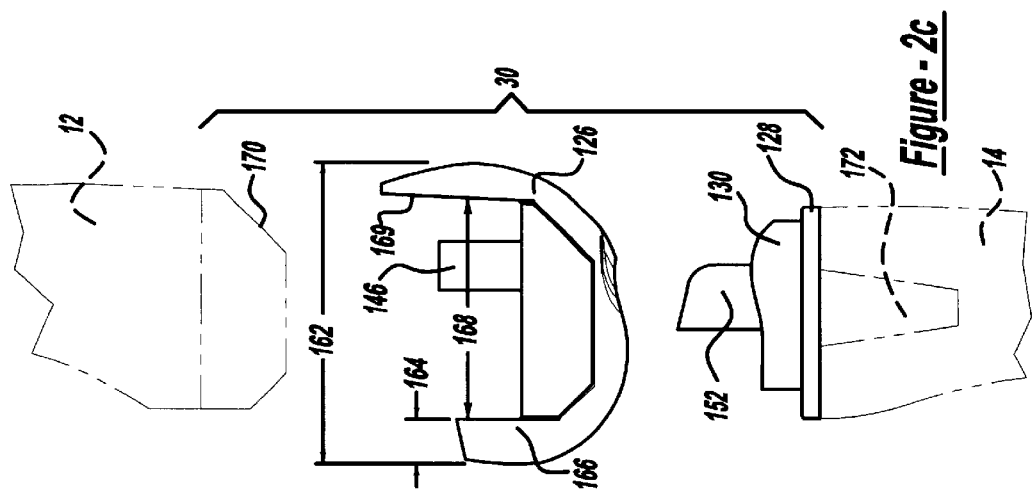
FIG. 2c is an exploded side view of a fully constrained knee joint prosthesis according to the teachings of the present invention.

The following description of the preferred embodiment(s) directed to providing an elongated femoral component for the posterior stabilized and the fully constrained knee joint prosthesis are merely exemplary in nature and are not intended to limit its application or uses. Moreover, while the present invention is described in detail below with respect to floating bearing type knee joint prostheses. Those skilled in the art will appreciate that the present invention is clearly not limited to only knee joint prostheses which employ floating bearings, but may be employed with any other type of knee joint prosthesis, such as a fixed bearing knee joint prosthesis.

Referring to FIG. 1, an anatomical knee joint 10 which provides articulating motion between a femur 12 and a tibia 14 is illustrated in detail. The anatomical knee joint 10 includes a posterior cruciate ligament (PCL) 16 and an anterior cruciate ligament (ACL) 18, which cross each other within the knee joint 10. The PCL and ACL ligaments 16 and 18 provide stability and strength to the knee joint 10. The knee joint 10 also includes a medial collateral ligament 20 and a lateral collateral ligament 22 used to balance the medial and lateral forces in the knee joint 10.

Figure 2B:
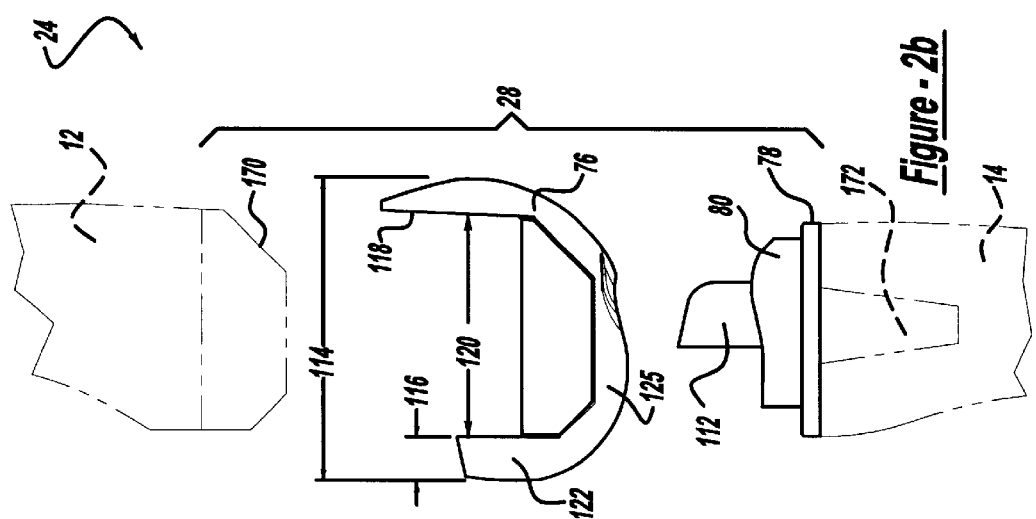
FIG. 2b is an exploded side view of a posterior stabilized (PS) knee joint prosthesis according to the teachings of the present invention.
Figure 2A:
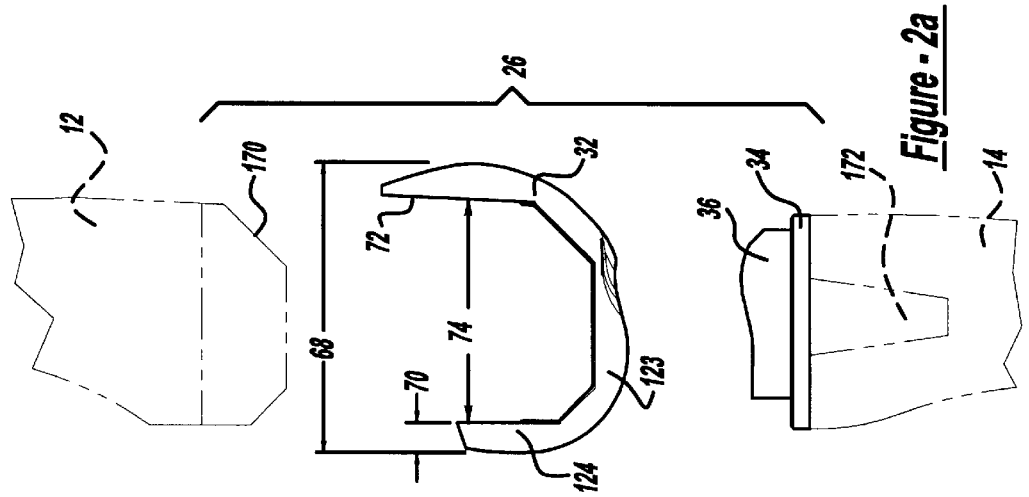
FIG. 2a is an exploded side view of a cruciate knee joint prosthesis according to the teachings of the present invention.
Figure 6:
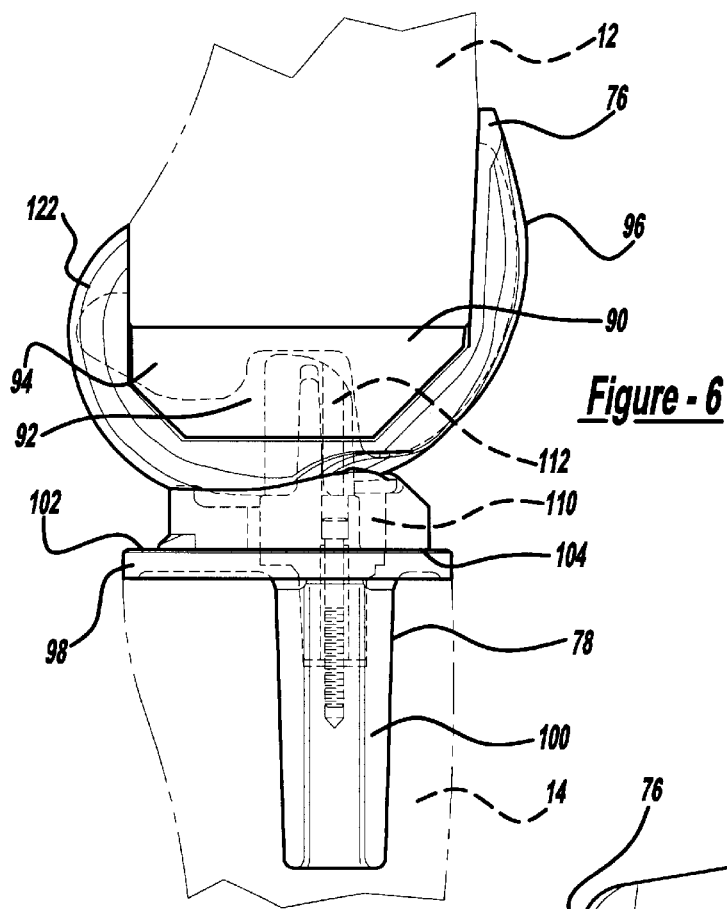
FIG. 6 is an assembled side view of the posterior stabilized (PS) knee joint prosthesis according to the teachings of the present invention.
Figure 7:
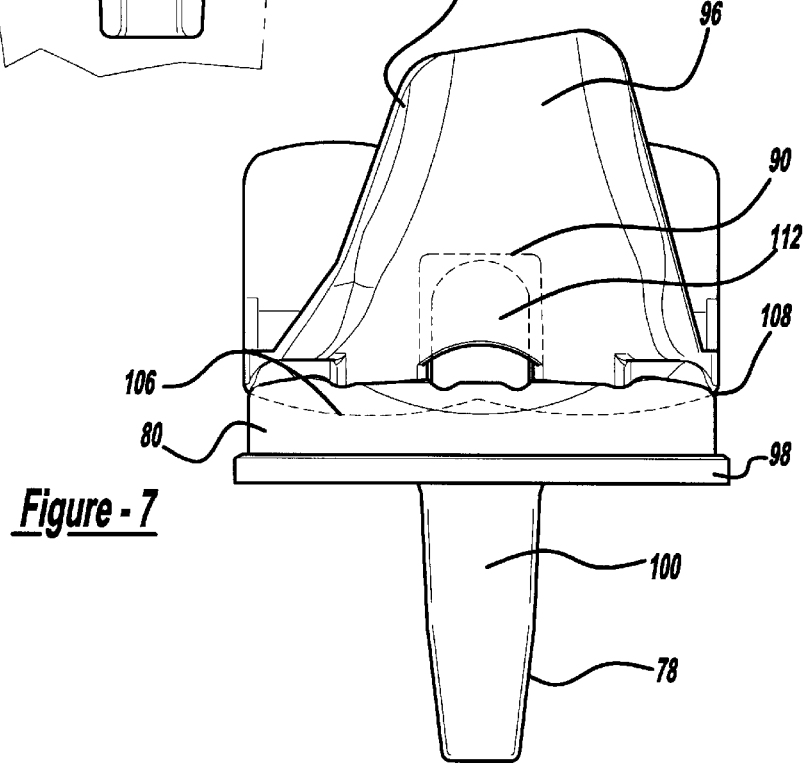
FIG. 7 is a front view of the posterior stabilized (PS) knee joint prosthesis according to the teachings of the present invention.

With reference to FIGS. 2a–2c, the knee joint prosthesis system 24 according to the teachings of the present invention is shown. The knee joint prosthesis system 24 generally includes a kit having a cruciate retaining (CR) knee joint prosthesis 26 (see FIG. 2a), a posterior stabilized (PS) knee joint prosthesis 28 (see FIG. 2b), and a fully constrained knee joint prosthesis 30 (see FIG. 2c). Each knee joint prostheses in the knee joint prosthesis system 24 provides a varying level of constraint with each being selected depending upon the patient's needs and the anatomical make-up of the particular patient. In this regard, should the anterior and posterior cruciate ligaments 18 and 16 not be sacrificed during the surgical procedure, a cruciate retaining (CR) knee joint prosthesis 26 will generally be employed which provides the least level of constraint. Should the anterior and posterior cruciate ligaments 16 and 18 be sacrificed or are dysfunctional and the medial and lateral collateral ligaments 20 and 22 remain functionally intact, the posterior stabilized (PS) knee joint prosthesis 28 will typically be employed which provides a higher level of constraint. Should both the anterior and posterior cruciate ligaments 18 and 16 be sacrificed and the medial and lateral collateral ligaments 20 and 22 be sacrificed or dysfunctional, the fully constrained knee joint prosthesis 30 will typically be employed, which provides the greatest level of constraint due to the sacrifice or loss of additional soft tissue ligaments.

It should be understand that the novel features of the knee joint prosthesis system 24 may be applied to any number of knee joint prostheses currently in existence, such as a fixed bearing or floating bearing type knee. For example, a fixed bearing type knee, such as that disclosed in U.S. Pat. No. 5,330,534, may employ the novel features of the present invention and is hereby incorporated by reference. Should a floating bearing knee joint prosthesis be employed, the floating bearing knee as disclosed in U.S. Pat. No. 6,165,223 or the floating bearing knee as disclosed in U.S. Ser. No. 09/695,448, filed Oct. 20, 2000, entitled "Floating Bearing Knee Joint Prosthesis With A Fixed Tibial Post" may also be employed, each of which are hereby incorporated by reference.

Accordingly, the novel features disclosed with the knee joint prosthesis 24 may be employed with any type of knee joint prosthesis currently in existence to provide a surgeon with interoperative options for selection of a proper level of constraint, while addressing the concern of an increased flexion gap should the posterior cruciate ligament 16 be sacrificed. This selectability will also be available without the need for further bone resection once the femur 12 has been properly resected for fitting with trial prostheses, which are known in the art and will be further discussed herein. In this regard, the present knee joint prosthesis system 24 provides equal distal and posterior condyle thickness' for the cruciate retaining knee joint prosthesis 26, but within the same system 24, the posterior stabilized knee joint prosthesis 28 and the fully constrained knee joint prosthesis 30 provide a thicker posterior condyle thickness than the distal condyle thickness. This provides the advantage of equalizing the collateral ligament tensions from extension to flexion after the PCL 16 is removed. This compares to current practices where a surgeon will typically "upsize" the femoral component and maintain the anterior reference and the anterior placement of the component, thereby oftentimes providing a femoral component that is too large in the medial to lateral dimension which may over extend the femur 12.

Referring now to FIGS. 2a, 3 and 4, the cruciate retaining knee joint prosthesis 26 will be discussed in detail. The cruciate retaining (CR) knee joint prosthesis 26 is shown to be secured to the femur 12 and the tibia 14 of a surgically resected left knee joint, with the femur 12 and the tibia 14 shown in phantom, and with the understanding that a suitable right knee joint prosthesis can be similarly constructed. The cruciate retaining (CR) knee joint prosthesis 26 includes a femoral component 32, a tibial component 34 and a floating tibial bearing 36.

The femoral component 32 is adapted to be secured to the distal end of the femur 12 and includes a first condylar portion 38 and a second condylar portion 40 that provides a first femoral bearing surface 42 and a second femoral bearing surface 44, respectively. The first and second condylar portions 38 and 40 of the femoral component 32 are interconnected by an intercondylar portion 46 that defines an inner condylar opening 48 to accommodate for the anterior and the posterior cruciate ligaments 16 and 18. The femoral component 32 also includes an arcuate patellar portion 50, which is disposed on the anterior surface of the femoral component 32. The patellar portion 50 is shaped to allow anatomical tracking of a natural or a prosthetic patella. The patella prosthesis, which are compatible with the present invention may be of varying shape, such as round or dome shaped and may be constructed from polyethylene, polyethylene with metal backing, or other suitable materials. The femoral component 32 is formed as a unitary structure and preferably cast of a biocompatible high strength alloy, such as cobalt-chromium-molybdenum alloy or other suitable material. All surfaces, which do not contact the femur 12, are preferably highly polished to provide smooth articulating bearing surfaces.

The tibial component 34 is adapted to be secured to the proximal end of the tibia 14 after the tibia 14 has been resected in a manner known in the art. The tibial component 34 includes a substantially planar platform-like tibial tray 52 and an inferior extending tibial stem 54. The tibial stem 54 is adapted to be received in a corresponding opening made by a surgeon in the longitudinal center of the tibial 14. The tibial tray 52 and the tibial stem 54 are preferably manufactured from cobalt-chromium-molybdenum or other suitable biocompatible material. The top of the tibial tray 52 is highly polished to provide a substantially smooth tibial bearing surface 56.

The floating or rotating bearing 36 is located between the femoral component 32 and the tibial component 34. The floating bearing 36 has a substantially planar inferior bearing surface 58, which slidably moves relative to the highly polished tibial bearing surface 56. The floating bearing 36 also includes a first superior articulating or bearing surface 60 and a second superior articulating or bearing surface 62. The first bearing surface 60 and the second bearing surface 62 articulate with the first bearing surface 42 of the first condylar portion 38 and the second bearing surface 44 of the second condylar portion 40 of the femoral component 32. Positioned between the first and second bearing surfaces 60 and 62 is a substantially rectangular opening 64 that is slidably positioned about a center modular guide post 66 which is secured to the tibial tray 52 by any appropriate means, such as a Morse taper with a screw. The opening 64 and the post 66 are sized to permit anterior to posterior, medial to lateral and rotational movement of the bearing 36. The center guide post 66 preferably does not extend beyond the bearing 36 and is preferably formed from a combination of a cobalt-chromium-molybdenum portion and a molded polymer portion formed from UHMWPE or other suitable material. The bearing 36 is preferably formed from a surgical grade, low pressure, low wearing plastic, such as UHMWPE or other suitable material.

The femoral component 32 has an overall anterior to posterior dimension 68 and a posteriorly condyle thickness 70, further discussed herein. The femoral component 32 is also referenced from the anterior point 72 to provide an anterior to posterior resection or mating area or dimension 74. As was previously indicated, the cruciate retaining (CR) femoral knee joint prosthesis 26 is generally employed when the anterior and posterior cruciate ligaments 18 and 16 are retained during a surgical procedure and therefore provides the least level of constraint. By retaining the posterior cruciate ligament 16, the flexion gap generally does not increase between the femur 12 and the tibia 14 during flexion and the extension gap also does not undergo any noticeable change.

Referring now to FIGS. 2b and 5–7, the posterior stabilized (PS) knee joint prosthesis 28 is shown and discussed in further detail. Here again, the posterior stabilized (PS) knee joint prosthesis 28 is generally employed when the anterior and posterior cruciate ligaments 18 and 16 are sacrificed, thereby providing an additional level of constraint due to loss of these particular ligaments.

The posterior stabilized (PS) knee joint prosthesis 28 includes a femoral component 76, a tibial component 78 and a bearing component 80. Here again, the femoral component 76 includes a first condylar portion 82, a second condylar portion 84 having a first bearing surface 86 and a second bearing surface 88, respectively. The first and second condylar portions 82 and 84 are interconnected by an intercondylar portion 90 that defines an intercondylar recess 92 and a cam or lobe 94. The intercondylar portion 90 essentially defines an intercondylar box which houses the lobe or cam 94, further discussed herein. The femoral component 76 also includes an arcuate patellar portion 96 which is disposed on the anterior surface of the femoral component 76, which is shaped to allow anatomical tracking of a natural or a prosthetic patellar. Here again, the femoral component 76 is preferably formed as a unitary structure and preferably cast of a biocompatible high strength alloy, such as cobalt-chromium-molybdenum allow or other suitable material. All surfaces, which do not contact the femur 12, are also preferably highly polished to provide smooth articulating bearing surfaces.

The tibial component 78 is substantially similar or the same as the tibial component 34 and is adapted to be secured to the proximal end of the tibia 14 after the tibia 14 has been resected in a manner known in the art. The tibial component 78 includes a substantially planar platform-like tibial tray 98 and an inferiorly extending tibial stem 100. The tibial stem 100 is again adapted to be received in a corresponding opening made by a surgeon in a longitudinal center of the tibia 14 and the tibial tray 98 is highly polished to provide a substantially smooth tibial bearing surface 102. The tibial component 78 is preferably manufactured from cobalt-chromium-molybdenum or other suitable biocompatible material.

The floating or rotating bearing 80 is positioned between the femoral component 76 and the tibial component 78. The floating bearing 80 includes a substantially planar inferior bearing surface 104 and first and second superior articulating bearing surfaces 106 and 108. Located between the first and second bearing surfaces 106 and 108 is a substantially rectangular opening 110 that is slidably positioned about a center modular guide post 112 which extends up through the rectangular opening 110. The opening 110 provides for anterior to posterior, medial to lateral, and rotational movement of the bearing 80 relative to the tibial tray 98, but is somewhat more constrained than the opening 64 associated with the cruciate retaining knee joint prosthesis 26. Here again, the bearing 20 is preferably formed from UHMWPE or other suitable material.

The center guide post 112 has a substantially oval shaped outer peripheral sidewall or any other appropriately shaped sidewall that enables anterior to posterior, as well as medial to lateral and rotational movement of the bearing 80 relative to the tibial tray 98. Also, the center guide post 112 extends superiorly into the intercondylar recess 92 of the intercondylar portion 90 to engage the cam or lobe 94 during flexion. In this regard, when the posterior stabilized (PS) knee joint prosthesis 28 is in flexion, the engagement of the guide post 112 relative to the lobe or cam 94 forces the bearing component 80, as well as the femoral component 76 to provide for a more natural anatomical femoral rollback, as discussed in detail in U.S. Pat. No. 6,165,223, and as disclosed in U.S. Ser. No. 09/695,448, filed Oct. 20, 2000, entitled "Floating Bearing Knee Joint Prosthesis With A Fixed Tibial Post", which are each hereby incorporated by reference.

Referring back to FIG. 2b, the femoral component 76 includes an anterior to posterior dimension 114 and a posterior condyle thickness 116. The femoral component 76 further includes an anterior reference point 118 and an anterior to posterior resection or femoral mating area or dimension 120. A posterior condylar region 122 of the femoral component 76 has a substantially larger posterior condylar thickness 116 as compared with the posterior condylar region 124 of the femoral component 32 which has the posterior condylar thickness 70. The posterior thickness 70 is about 8 mm, while the posterior thickness 116 is about 8 to 16 mm. The distal condylar thickness of the distal regions 123 and 125 of the cruciate retaining (CR) femoral component 32 and the posterior stabilized (PS) femoral component 76 are substantially the same. Also, the posterior condylar thickness 70 of the cruciate retaining (CR) femoral component 32 is substantially the same as the distal condylar thickness of the distal region 123.

During a surgical procedure, should a surgeon pre-operatively determine to use the cruciate retaining (CR) knee joint prosthesis 26, the surgeon will typically resect the tibia 14 and implant the tibial component 34. The surgeon will then generally resect the femur 12 and either uses a trial component (not shown) or the femoral component 32 having the resection mating area 74. If, during the surgical procedure, a surgeon determines that the posterior cruciate ligament 16 must be sacrificed, the femoral component 32 will not provide a large enough thickness in the posterior condylar region 124 to accommodate for the increased flexion gap by removal of the posterior cruciate ligament 16. To accommodate for this interoperative decision, the posterior stabilized (PS) femoral component 76 may simply be utilized in place of the cruciate retaining (CR) femoral component 32 since the resection mating area 120 of the femoral component 76 is substantially identical to the resection mating area 74 of the femoral component 32.

In this regard, the anterior reference points 72 and 118 of each femoral component 32 and 76 is the same with the posterior stabilized (PS) femoral component 76 providing a thicker posterior condyle portion 122, identified as reference numeral 116 that extends further posteriorly. Therefore, the anterior to posterior dimensions 74 and 120 are substantially the same, with the understanding that a femoral cut to accommodate the intercondylar portion 90 may be required. Likewise, the guide post 66 in the tibial component 34 may be simply replaced with the guide post 112, as well as the bearing 80 in place of the bearing 32, which provides for a smaller opening 110 providing a further level of constraint. This way, a surgeon can simply interoperatively select either the cruciate retaining (CR) knee joint prosthesis 26 or the posterior stabilized (PS) knee joint prosthesis 28 without having to perform any further adjustments or anterior to posterior resections to the femur 12 or tibia 14. The only femoral cut that may be necessary is to accommodate for the intercondylar portion 90. In this way, the flexion gap typically associated with PCL removal is adequately accommodated with the posterior stabilized (PS) femoral component 76. In contrast, with existing systems, a surgeon would typically either require a posterior condylar augment by upsizing the femoral component, such that there may be medial and lateral overhang of the component relative to the femur 12, which is an undesirable condition or further anterior to posterior cuts may be required.

Figure 8:
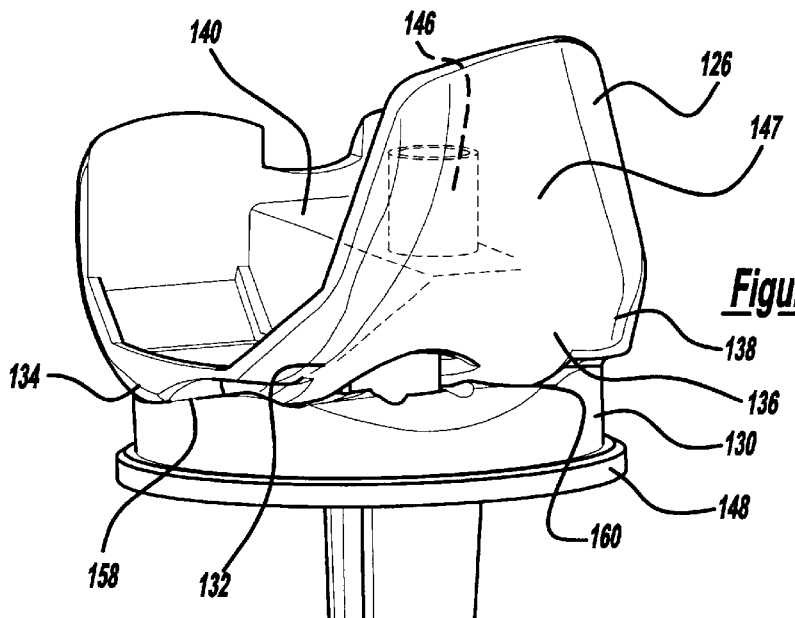
FIG. 8 is a perspective view of the fully constrained knee joint prosthesis according to the teachings of the present invention.
Figure 9:
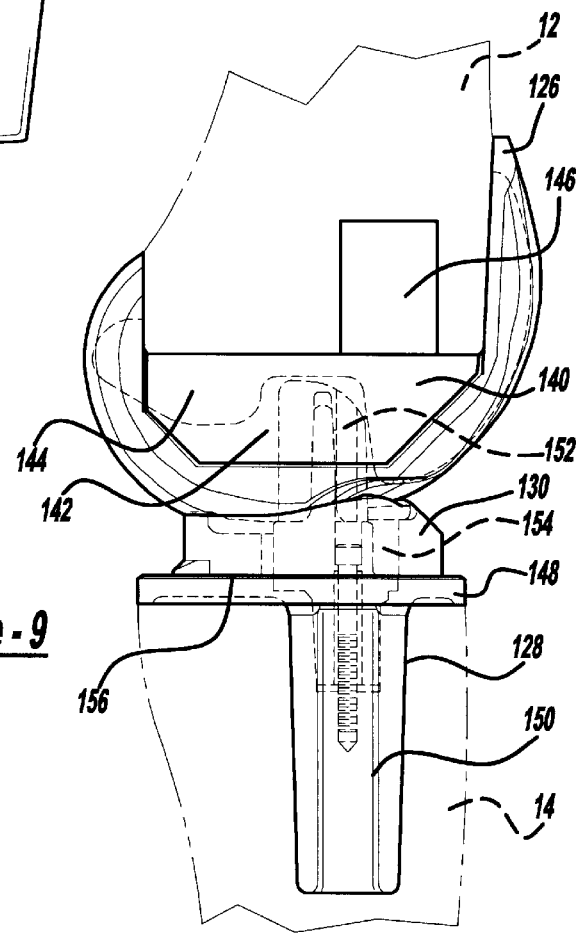
FIG. 9 is an assembled side view of the fully constrained knee joint prosthesis according to the teachings of the present invention.

Finally, referring to FIGS. 2c, 8 and 9, the fully constrained knee joint prosthesis 30 is shown in further detail. In this regard, the fully constrained knee joint prosthesis system 30 is substantially similar to the posterior stabilized (PS) knee joint prosthesis 28 except for a few slight modifications. The fully constrained knee joint prosthesis 30 again includes a femoral component 126, a tibial component 128 and a bearing 130. The femoral component 126 again includes a first condylar portion 132 having a first bearing surface 134 and a second condylar portion 136 having a second bearing surface 138. An intercondylar portion 140 interconnects the first and second condylar portions 132 and 134 which also defines an intercondylar recess 142 having a cam lobe 144. Extending superiorly from the intercondylar portion 140 is a substantially cylindrical stem 146, which provides further support for the fully constrained femoral component 126. A patella surface 147 is also provided anteriorly of the femoral component 126.

The tibial component 128 is the same or substantially similar to the tibial components 34 and 78 and again includes a tibial plateau 148, and an inferior extending stem 150. Removably attached to the tibial component 128 is a guidepost 152, which extends up through a recess 154 in the bearing 130. The bearing 130 again includes the inferior bearing surface 156, and the first and second superior articulating bearing surfaces 158 and 160.

The fully constrained knee joint prosthesis 30 is substantially similar to the posterior stabilized knee joint prosthesis 28, except that it provides the further stabilizing cylindrical stem 146, as well as provides and defines a smaller opening 154 within the bearing 130. This smaller opening 154 engages the medial and lateral sidewalls of the guide posts 152 to provide for only anterior to posterior movement of the bearing 130 relative to the tibial plateau 148. The medial to lateral constraint is provided since the medial and collateral ligaments 20 and 22 are generally removed when the fully constrained knee joint prosthesis 30 is employed.

Here again, the femoral component 126 includes an anterior to posterior dimension 162 and posterior condyle thickness 164 for the posterior condylar portion 166 and an anterior to posterior resecting mating area or dimension 168 that start at anterior reference point 169. The anterior to posterior dimension 162, the posterior thickness 164, the anterior to posterior resection/mating area or dimension 168, and the distal condylar thickness are substantially the same as the corresponding dimensions in the posterior stabilized femoral component 76.

Additionally, it should be noted that the anterior to posterior resection mating area or dimensions 74, 120 and 168 are substantially the same for each knee joint prosthesis 26, 28 and 30, along with the distal condylar thickness. In this regard, only the posterior stabilized (PS) knee joint prosthesis 28 and the fully constrained knee joint prosthesis 30 provides additional posterior thickness 116 and 164 which are greater than the posterior thickness 70 in the cruciate retaining (CR) knee joint prosthesis 26 to accommodate for the increased flexion gap. This increased thickness comes as a result of adding additional material posteriorly, as opposed to providing further removal of femoral bone, thereby enabling the anterior to posterior resecting mating area or dimension for each knee joint prosthesis to be substantially the same, as well as the distal condylar thickness of each knee joint prosthesis. This enables a surgeon to interoperatively select between either the cruciate retaining (CR) knee joint prosthesis 26, the posterior stabilized (PS) knee joint prosthesis 28 or the fully constrained knee joint prosthesis 30 without having to further resect the femur 12, except to account for the intercondylar portions 90 and 140, and also provide for a thicker posterior condyle region to accommodate for flexion gap increases should the posterior cruciate ligament 16 be removed. This provides the advantage of equalizing the collateral ligament tensions in the posterior stabilized (PS) knee joint prosthesis 30 from extension to flexion after the posterior cruciate ligament 16 is surgically removed. This also maintains the anterior reference point and the anterior placement of each femoral component.

In operation, preoperatively, the surgeon will select whether to use a cruciate retaining (CR) knee joint prosthesis 26, the posterior stabilized (PS) knee joint prosthesis 28 or the fully constrained knee joint prosthesis 30. If the surgeon has pre-selected the cruciate retaining (CR) knee joint prosthesis 26, the end of the femur 12 will be resected and the surgeon will form a resected engagement surface 170 with the intention of implanting the first femoral component 32 having a corresponding resection/mating region or dimension 74. The end of the tibia 14 is also resected to cooperatively engage the tibial component 34. A passageway 172 is also formed in the tibia 14 and the stem 54 is inserted into the passageway 172 as is conventional. The bearing 36 is placed between the tibial tray 52 and the first femoral component 32.

If interoperatively in trial, the surgeon determines that the natural knee joint 10 is found to be more severely deformed or dysfunctional than it was preoperatively thought to be, the surgeon must make a decision about whether or not to resect the posterior cruciate ligament (PCL) 16. Some surgeons will attempt to preserve the posterior cruciate ligament (PCL) 16 if at all possible, while others prefer preservation in only selected cases where there is less deformity in the knee joint 10. If satisfactory soft tissue balance cannot be obtained, the surgeon will consider changing from a cruciate retaining (CR) knee joint prosthesis 26 to a posterior stabilized (PS) knee joint prosthesis 28. If the surgeon decides not to resect the PCL 16, the surgeon will continue with the procedure and retain the first femoral component 32, the bearing 36 and the tibial component 34, in the knee joint 10 as is conventional.

If the posterior cruciate ligament 16 is resected, the surgeon will be confronted with the need to compensate for an increase in flexion gap. To compensate for the increase in flexion gap, the surgeon will remove the first (CR) femoral component 32 and instead implant the second (PS) femoral component 76. Since the resecting/mating region 120 of the second femoral component 70 is the same as the resecting/mating region 74 of the first femoral component 32, the surgeon will not be required to resect the end of the femur 12 as the resected engagement surface 170 will cooperatively engage the engagement region 120. Only resection to accommodate for the intercondylar portion 90 will be required which does not change the shape of the resected engagement surface 170. This saves time and reduces the complexity of the surgical procedure for the surgeon.

The second femoral component 76 has the larger posterior condylar thickness 116 than a distal condylar thickness 174 in order to compensate for the increase in flexion gap which could be between 4 mm to 8 mm. The required size of the posterior condylar thickness 116 is selected by the surgeon to balance the flexion and extension in the knee joint 10. The posterior condylar thickness 116 is in the range of about 8 to 16 mm and the distal condylar thickness 174 is between about 8 to 9 mm. This eliminates the need to compromise the range of motion of the knee joint prosthesis or require further surgical resectioning of the femoral engagement surface.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A knee joint prosthesis system adapted to replace the articulating knee portion of a femur and a tibia, the femur having a resected engagement surface, said knee joint prosthesis system comprising:

a first femoral component having a first femoral engagement region and at least a first condylar portion having a first femoral bearing surface, said first femoral engagement region operable to engage the resected engagement surface of the femur and said first condylar portion including a first posterior region having a first thickness; and a second femoral component having a second femoral engagement region and at least a second condylar portion having a second femoral bearing surface, said second femoral engagement region operable to engage the resected engagement surface of the femur and said second condylar portion including a second posterior region having a second thickness, wherein said second thickness is larger than said first thickness and said first femoral engagement region is substantially the same as said second femoral engagement region, wherein said first femoral component has an outer anterior to posterior length that is less than an outer anterior to posterior length of said second femoral component, whereby a surgeon may select one of said first femoral component and said second femoral component for attachment to the femur.

2. The knee joint prosthesis system as defined in claim 1 further comprising a tibial component operable to be attached to the tibia and having a tibial bearing surface.

3. The knee joint prosthesis system as defined in claim 2 further comprising a bearing member operable to be positioned between one of said first and second femoral components and said tibial component.

4. The knee joint prosthesis system as defined in claim 3 wherein said bearing member is selected from a group consisting of a fixed bearing and a mobile bearing.

5. The knee joint prosthesis system as defined in claim 1 wherein said second thickness ranges between about 8 mm to about 16 mm.

6. The knee joint prosthesis system as defined in claim 1 wherein said first femoral component is a first cruciate femoral component and said second femoral component is a second posterior stabilized (PS) femoral component.

7. The knee joint prosthesis system as defined in claim 1 wherein said first femoral component is a first cruciate femoral component and said second femoral component is a second fully constrained femoral component.

8. A knee joint prosthesis system adapted to replace the articulating knee portion of a femur and a tibia, the femur having a resected engagement surface, said knee joint prosthesis system comprising:

a first femoral component having a first femoral engagement region and at least a first condylar portion having a first femoral bearing surface, said first femoral engagement region operable to engage the resected engagement surface of the femur and said first condylar portion including a first posterior region having a first thickness; and a second femoral component having a second femoral engagement region and at least a second condylar portion having a second femoral bearing surface, said second femoral engagement region operable to engage the resected engagement surface of the femur and said second condylar portion including a second posterior region having a second thickness, wherein said second thickness is larger than said first thickness and said first femoral engagement region is substantially the same as said second femoral engagement region, and wherein said first femoral engagement region and said second femoral engagement region has substantially the same inner anterior to posterior dimension, whereby a surgeon may select one of said first femoral component and said second femoral component for attachment to the femur.

9. A knee joint prosthesis system adapted to replace the articulating knee portion of a femur and a tibia, the femur having a resected engagement surface, said knee joint prosthesis system comprising:

a first femoral component having a first femoral engagement region and at least a first condylar portion having a first femoral bearing surface, said first femoral engagement region operable to engage the resected engagement surface of the femur and said first condylar portion including a first posterior region having a first thickness; and a second femoral component having a second femoral engagement region and at least a second condylar portion having a second femoral bearing surface, said second femoral engagement region operable to engage the resected engagement surface of the femur and said second condylar portion including a second posterior region having a second thickness, wherein said second thickness is larger than said first thickness and said first femoral engagement region is substantially the same as said second femoral engagement region, and wherein said first femoral component includes a first distal region having a third thickness and said second femoral component includes a second distal region having a fourth thickness, said first thickness being substantially equal to said third thickness and said fourth thickness, whereby a surgeon may select one of said first femoral component and said second femoral component for attachment to the femur.

10. A knee joint prosthesis system adapted to replace the articulating knee portion of a femur and a tibia, the femur having a resected engagement surface, the knee joint prosthesis system comprising:

a cruciate retaining (CR) femoral component having a first femoral engagement region and at least a first condylar portion having a first femoral bearing surface, said first femoral engagement region operable to engage the resected engagement surface of the femur and said first condylar portion including a first posterior region having a first thickness and a first distal region having a second thickness, said first thickness being substantially equal to said second thickness; and a posterior stabilized (PS) femoral component having a second femoral engagement region and at least a second condylar portion having a second femoral bearing surface, said second femoral engagement region operable to engage the resected engagement surface of the femur and said second condylar portion including a second posterior region having a third thickness and a second distal region having a fourth thickness, said third thickness being greater than said fourth thickness, said first femoral engagement region being substantially the same as said second femoral engagement region and, wherein said cruiciate retaining (CR) femoral component has an outer anterior to posterior length that is less than an outer anterior to posterior length of said posterior stabilized (PS) femoral component, whereby a surgeon may select one of said cruciate retaining (CR) femoral component and said posterior stabilized (PS) femoral component, whereby said posterior stabilized (PS) femoral component will accommodate for an increased flexion gap upon resection of a posterior cruciate ligament.

11. The knee joint prosthesis system as defined in claim 10 further comprising a tibial component operable to be attached to the tibia and having a tibial bearing surface.

12. The knee joint prosthesis system as defined in claim 11 further comprising a bearing member operable to be positioned between one of said cruciate retaining (CR) and said posterior stabilized (PS) femoral component and said tibial component.

13. The knee joint prosthesis system as defined in claim 12 wherein said bearing member is selected from a group consisting of a fixed bearing and a mobile bearing.

14. The knee joint prosthesis system as defined in claim 10 wherein said third thickness ranges between about 8 mm to about 16 mm.

15. A knee joint prosthesis system adapted to replace the articulating knee portion of a femur and a tibia, the femur having a resected engagement surface, the knee joint prosthesis system comprising:

a cruciate retaining (CR) femoral component having a first femoral engagement region and at least a first condylar portion having a first femoral bearing surface, said first femoral engagement region operable to engage the resected engagement surface of the femur and said first condylar portion including a first posterior region having a first thickness and a first distal region having a second thickness, said first thickness being substantially equal to said second thickness; and a posterior stabilized (PS) femoral component having a second femoral engagement region and at least a second condylar portion having a second femoral bearing surface, said second femoral engagement region operable to engage the resected engagement surface of the femur and said second condylar portion including a second posterior region having a third thickness and a second distal region having a fourth thickness, said third thickness being greater than said fourth thickness, said first femoral engagement region being substantially the same as said second femoral engagement region, and wherein said first femoral engagement region and said second femoral engagement region has substantially the same inner anterior to posterior dimension, whereby a surgeon may select one of said cruciate retaining (CR) femoral component and said posterior stabilized (PS) femoral component, whereby said posterior stabilized (PS) femoral component will accommodate for an increased flexion gap upon resection of a posterior cruciate ligament.

16. A knee joint prosthesis system adapted to replace the articulating knee portion of a femur and a tibia, the femur having a resected engagement surface, the knee joint prosthesis system comprising:

a cruciate retaining (CR) femoral component having a first femoral engagement region and at least a first condylar portion having a first femoral bearing surface, said first femoral engagement region operable to engage the resected engagement surface of the femur and said first condylar portion including a first posterior region having a first thickness and a first distal region having a second thickness, said first thickness being substantially equal to said second thickness; and a posterior stabilized (PS) femoral component having a second femoral engagement region and at least a second condylar portion having a second femoral bearing surface, said second femoral engagement region operable to engage the resected engagement surface of the femur and said second condylar portion including a second posterior region having a third thickness and a second distal region having a fourth thickness, said third thickness being greater than said fourth thickness, said first femoral engagement region being substantially the same as said second femoral engagement region, and wherein said first thickness, said second thickness and said fourth thickness are substantially the same thickness, whereby a surgeon may select one of said cruciate retaining (CR) femoral component and said posterior stabilized (PS) femoral component, whereby said posterior stabilized (PS) femoral component will accommodate for an increased flexion gap upon resection of a posterior cruciate ligament.

17. A method for implanting a femoral component to a femur having a resected engagement surface from a knee joint prosthesis system, said method comprising:

resecting the femur to provide the resected engagement surface;

providing a first femoral component having a first condylar portion which includes a first posterior region having a first thickness and a first femoral engagement region and second femoral component having a second condylar portion which includes a second posterior region having a second thickness and a second femoral engagement region where said second thickness is greater than said first thickness and wherein said first femoral engagement region and said second femoral engagement region has substantially the same inner anterior to posterior dimension; and intraoperatively determining if a posterior cruciate ligament should be removed;

if the posterior cruciate ligament is retained, selecting the first femoral component;

if the posterior cruciate ligament is removed, selecting the second femoral component which will accommodate for an increased flexion gap upon resection of the posterior cruciate ligament.

18. The method as defined in claim 17 wherein the first femoral component is a cruciate femoral component and the second femoral component is a posterior stabilized femoral component.

* * * * *

UNITED STATES PATENT AND TRADEMARK OFFICE
CERTIFICATE OF CORRECTION

PATENT NO.      : 6,589,283 B1
DATED           : July 8, 2003
INVENTOR(S)     : Metzger et al.

It is certified that error appears in the above-identified patent and that said Letters Patent is hereby corrected as shown below:

<u>Title page,</u>
Item [*] Notice: Subject to any disclaimer, the term of this patent is extended or adjusted under 35 USC 154(b) by (7) days
Delete the phrase "by 7 days" and insert -- by 58 days --

Signed and Sealed this

Twenty-fifth Day of November, 2003

JAMES E. ROGAN
*Director of the United States Patent and Trademark Office*